United States Patent [19]

Curie et al.

[11] Patent Number: 5,378,240
[45] Date of Patent: Jan. 3, 1995

[54] SYRINGE WITH RETRACTABLE NEEDLE MOUNT

[76] Inventors: Napoleon Curie, 32 Cliff Road, Frankston, Victoria, 3199; David N. Mason, 323 South Gippsland Highway, Cranbourne, Victoria, 3977, both of Australia

[21] Appl. No.: 856,065
[22] PCT Filed: Nov. 8, 1990
[86] PCT No.: PCT/AU90/00537
§ 371 Date: May 8, 1992
§ 102(e) Date: May 8, 1992
[87] PCT Pub. No.: WO91/07198
PCT Pub. Date: May 30, 1991

[30] Foreign Application Priority Data

Nov. 8, 1989 [AU] Australia .................. PJ7281/89

[51] Int. Cl.⁶ .................................. A61M 5/00
[52] U.S. Cl. ........................................ 604/110
[58] Field of Search ............... 604/110, 194, 195, 196, 604/197, 198, 218, 220

[56] References Cited

U.S. PATENT DOCUMENTS

| | | |
|---|---|---|
| 3,306,290 | 2/1967 | Weltman . |
| 3,478,937 | 11/1969 | Solowey . |
| 3,735,761 | 5/1973 | Hurschman et al. ............ 604/196 X |
| 3,797,490 | 3/1974 | Hurschman et al. ............ 604/196 X |
| 3,797,491 | 3/1974 | Hurschman et al. ............ 604/196 X |
| 3,810,649 | 5/1974 | Hurschman et al. ............ 604/196 X |
| 3,820,542 | 6/1974 | Hurschman .................... 604/196 |
| 3,890,971 | 6/1975 | Leeson et al. . |
| 4,026,287 | 5/1977 | Haller . |

(List continued on next page.)

FOREIGN PATENT DOCUMENTS

| | | |
|---|---|---|
| 77054/81 | 5/1983 | Australia . |
| 10257/88 | 1/1988 | Australia . |
| 11436/88 | 8/1988 | Australia . |
| 13088/88 | 9/1988 | Australia . |
| 14189/88 | 10/1988 | Australia . |
| 15366/88 | 11/1988 | Australia . |
| 28334/89 | 7/1989 | Australia . |
| 28795/89 | 8/1989 | Australia . |
| 30004/89 | 8/1989 | Australia . |
| 24498/88 | 9/1989 | Australia . |
| 32673/89 | 10/1989 | Australia . |
| 0209976 | 1/1987 | European Pat. Off. . |
| 0321903 | 6/1989 | European Pat. Off. . |
| 0351541 | 1/1990 | European Pat. Off. . |
| 0360313 | 3/1990 | European Pat. Off. . |
| 0347742 | 12/1990 | European Pat. Off. . |
| WO89/00435 | 1/1989 | WIPO . |
| WO89/02287 | 3/1989 | WIPO . |
| WO89/02760 | 4/1989 | WIPO . |
| WO89/04681 | 6/1989 | WIPO . |
| WO89/09075 | 10/1989 | WIPO . |

*Primary Examiner*—Gene Mancene
*Assistant Examiner*—Thomas Price
*Attorney, Agent, or Firm*—Knobbe, Martens, Olson & Bear

[57] ABSTRACT

A syringe with a deformable portion is used to secure a needle mount within a barrel on the syringe. A shoulder inside the barrel prevents withdrawal of the needle mount from the barrel. The needle mount has a plurality of resilient, angularly spaced arms projecting into the barrel to engage a cooperative element on the inside of the barrel and retain the needle mount and needle. The plunger deforms the resilient arms to disengage the needle mount from the barrel, while engaging means on the plunger in turn engage snap lock portions on the resilient arms to withdraw the needle into the barrel with the plunger, where the plunger is captured and held.

11 Claims, 6 Drawing Sheets

U.S. PATENT DOCUMENTS

| | | |
|---|---|---|
| 4,188,950 | 2/1980 | Wardlaw . |
| 4,391,272 | 7/1983 | Staempfli . |
| 4,507,117 | 3/1985 | Vining et al. . |
| 4,542,749 | 11/1985 | Caselgrandi et al. . |
| 4,553,962 | 11/1985 | Brunet . |
| 4,562,844 | 1/1986 | Carpenter et al. . |
| 4,592,744 | 6/1986 | Jagger et al. . |
| 4,643,199 | 2/1987 | Jennings, Jr. et al. . |
| 4,643,200 | 2/1987 | Jennings, Jr. . |
| 4,650,468 | 3/1987 | Jennings, Jr. . |
| 4,675,005 | 6/1987 | DeLuccia . |
| 4,687,467 | 8/1987 | Cygielski .............................. 604/110 |
| 4,692,165 | 9/1987 | Haller . |
| 4,710,170 | 12/1987 | Haber et al. . |
| 4,747,830 | 5/1988 | Gloyer et al. . |
| 4,747,831 | 5/1988 | Kulli . |
| 4,767,413 | 8/1988 | Haber et al. . |
| 4,770,655 | 9/1988 | Haber et al. . |
| 4,790,822 | 12/1988 | Haining ................................. 604/110 |
| 4,804,370 | 2/1989 | Haber et al. . |
| 4,820,275 | 4/1989 | Haber et al. . |
| 4,826,484 | 5/1989 | Haber et al. . |
| 4,838,869 | 6/1989 | Allard . |
| 4,846,808 | 7/1989 | Haber et al. . |
| 4,888,002 | 12/1989 | Braginetz et al. . |
| 4,931,040 | 6/1990 | Haber et al. ......................... 604/110 |
| 4,950,241 | 8/1990 | Ranford . |
| 4,978,339 | 12/1990 | Labouze et al. .................... 604/110 |
| 4,994,034 | 2/1991 | Botich et al. . |
| 5,098,390 | 3/1992 | Wallingford ......................... 604/110 |

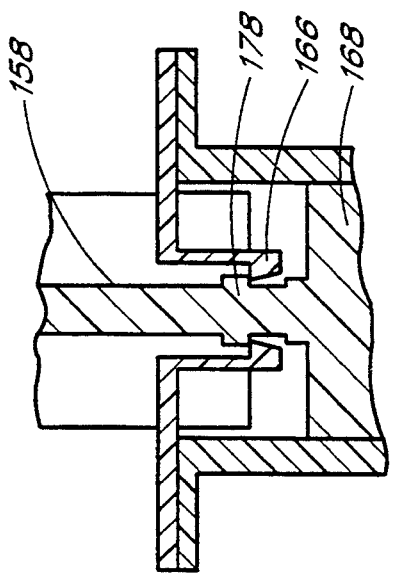
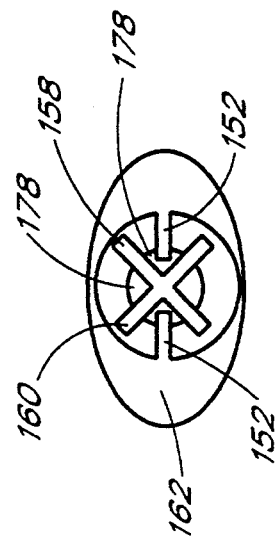
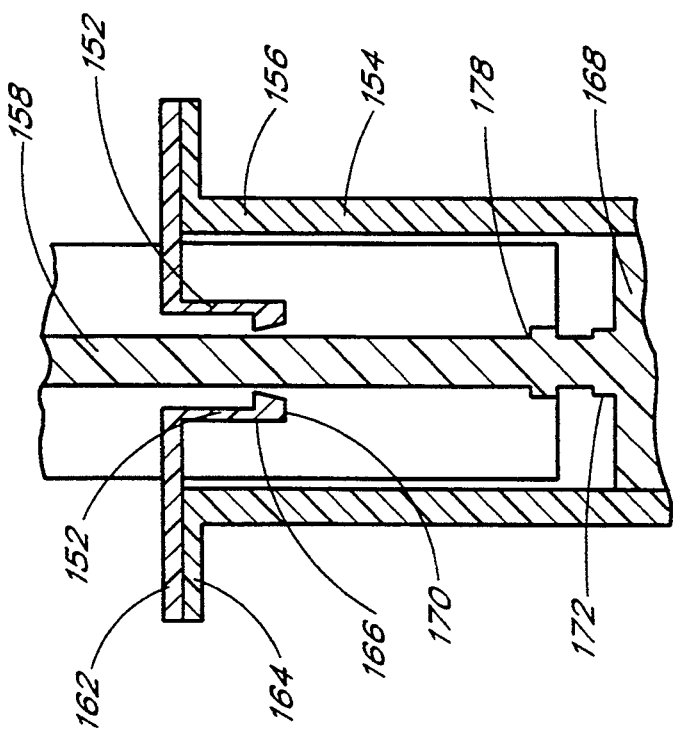

SYRINGE WITH RETRACTABLE NEEDLE MOUNT

This invention relates to syringes having a retractable needle mount.

BACKGROUND OF THE INVENTION

Preventing accidental injury and infection from used hypodermic needles has attracted considerable interest in recent years, however previous proposals to produce syringes which retract the needle into the barrel of the syringe have required inconvenient locking or disengagement steps to release the needle from its injecting position so as to allow it to be withdrawn into the barrel.

Of interest in U.S. Pat. No. 4,026,287 which describes an arrangement in which the plunger has a screw fitting on its forward face. When the plunger reaches its fully depressed position, it is rotated to allow the screw fitting on the plunger to engage a corresponding thread on a forward portion of the syringe barrel in which the needle is seated. After securing the needle in this fashion, the plunger is withdrawn thus severing a weakening between the barrel and the forward needle portion to allow retraction of the needle. The requirement to screw engage the plunger and needle necessitates additional hand movements while the potentially dangerous needle is still exposed and further, severing the forward needle portion from the barrel requires significant force.

Some previous proposals, for instance as shown in U.S. Pat. Nos. 4,692,156, 4,507,117 and 4,804,370 or PCT Publication Nos. WO89/04681 and WO89/09075 have utilized a snap connection between a fitting on the forward end of the plunger and a formation associated with the needle or its mounting. These arrangements allow engagement of the plunger and needle (mount) without a distinct locking or screwing step. However, in these arrangements the needle (mount) is adhered or force fit into sealing engagement with the barrel and force must be applied during retraction of the plunger to break this adhesive or other connection between the needle (mount) and the barrel. This is disadvantageous as not only does this rearward force need to be applied while the needle is exposed, but the engagement between the plunger and the needle (mount) must be robust enough to prevent unlocking of the needle (mount) during application of this force.

The syringes depicted in U.S. Pat. No. 4,838,869 and Australian Patent Application No. 28334/89 provide a more active release of the needle or its mount from the remainder of the barrel. In these syringes, the plunger, in its fully depressed position engages the forward wall of the barrel, adjacent the needle, thus breaking the adhesive or seal between the needle or its mount and the barrel allowing the needle (mount) to be retracted without applying a significant rearward force. These arrangements, however, are not amenable to easy production techniques and furthermore do not appear to be well adapted for syringes in which a removable needle is located on a needle seat of the needle mount.

The arrangement depicted in PCT Publication No. WO89/00435 also uses the downward motion of the plunger to disengage the needle from the barrel, in this case allowing it to be spring biased into a recess in the plunger. As with the syringes discussed in the immediately preceding paragraph, the arrangement shown in WO89/00435 is not amenable to easy mass production and furthermore is incapable of being used with a replaceable needle as is required, for instance, when a syringe is filled from an ampoule using a first needle but injected into a patient using a fresh sterile needle. A further disadvantage of the WO89/00435 syringe is the comparatively fragile nature of the seating of the needle in the barrel before retraction which is likely to prematurely retract the needle if the syringe is inadvertently inserted into unyielding material such as callous or muscle.

It is an object of the present invention to ameliorate some of the shortcomings evident in previous proposals to provide a syringe in which the needle mount is automatically engaged by the plunger for safe retraction into the barrel.

SUMMARY OF THE INVENTION

In accordance with the present invention there is provided a syringe comprising a barrel, a plunger operable within the barrel and a needle mount having a deformable securing portion to disengageably retain the needle mount at one end of the barrel, the securing portion comprising a first element of snap lock engaging means which cooperates with a second element of the snap lock engaging means on an interior wall of the barrel, the syringe further comprising means on the plunger to deform the securing portion as the plunger approaches the needle mount thereby to disengage the snap lock engagement of the needle mount with the barrel and cooperable means on the plunger and on the needle mount whereby the plunger is capable of engaging the disengaged needle mount for withdrawal of the needle mount into the barrel when the plunger or a portion thereof engaged with the needle mount is displaced away from said one end of the barrel.

The automatic disengagement of the needle mount securing portion from the barrel by the plunger as the syringe is emptied is particularly convenient as no additional operations need be performed to ensure such disengagement of the needle mount.

The snap lock engagement between the needle mount securing means and the barrel is advantageously configured to avoid the needle mount becoming inadvertently disengaged from the barrel even when the needle is inserted into comparatively unyielding objects. Most advantageously the first and second elements of the snap lock engaging means have cooperating surfaces oriented to prevent disengagement unless the securing means is actively deformed by the plunger. Conveniently the cooperating surfaces extend perpendicularly to the axis of the syringe.

Disengagement of the snap lock relationship between the securing portion and the interior wall of the barrel will typically involve the deformation of the first element of the snap lock means, on the securing portion, radially inward away from the interior wall of the barrel as the plunger descends. In one arrangement, the deforming means on the plunger is in the form of an inclined radially inwardly facing surface which bears on a projection on the securing portion during descent of the plunger thus displacing the securing portion radially inward. Alternatively, an upper surface of the securing portion engages a forward projection on the plunger defining the deforming means, the said upper surface being in the form of an inclined radially outwardly facing surface which is displaced radially inward by the projection during descent of the plunger. Conveniently the engagement surfaces on both the deforming means of the plunger and the securing portion have corresponding inclined surfaces (i.e. in the arrangements discussed immediately above the respective projections both have suitably inclined engagement surfaces).

In a preferred arrangement of the syringe the securing portion comprises a plurality of resilient angularly spaced arms projecting into the barrel, each arm having a respective first snap lock element thereon. The cooperable means on the needle mount for engaging the plunger is conveniently in the form of a catch on one or more of the arms.

A needle to be used with the syringe may be permanently secured to the needle mount but it is preferred that the needle mount has a seat to detachably receive the needle. This may allow the same syringe to be used with more than one needle before the needle mount is withdrawn as may occur if separate needles are used to respectively fill and discharge the syringe. Particularly where the needle mount is intended to receive a detachable needle, the engagement of the needle mount in the end of the barrel is preferably prevents rotation of the needle mount relative to the barrel, as could occur when locating the needle on the needle mount, is restrained. This restraint could take the form of a boss projecting from one portion of the needle mount engaging a cooperating groove extending axially in an interior wall of the barrel so as to prevent rotation of the needle mount. In this arrangement, the groove allows the boss to be displaced axially during withdrawal of the needle mount. Alternatively a projection could be disposed on the interior wall of the barrel to cooperate with a suitably shaped detent in the needle mount.

The syringe will preferably have means to prevent the plunger being entirely withdrawn from the barrel after disengagement and capture of the needle mount. Such withdrawal prevention can be provided by making the body of the plunger remote from its head of smaller diameter than the head, and further providing a projection extending into the barrel at the handle end of the barrel to engage the wider head portion of the plunger as it approaches the handle end of the barrel.

In a preferred embodiment of the invention, the cooperation between the plunger and the needle mount is such that the needle mount, when no longer retained within said one end of the barrel is permitted to cant over whereby the tip of a needle associated with the withdrawn needle mount is capable of engaging an inwardly projecting surface of the barrel to prevent the needle re-extending through said one end of the barrel. This can be achieved by providing catch means on the securing means at the forward end of the plunger to capture the released needle mount, the respective catch means being disposed asymmetrically with respect to the axis of the syringe. Conveniently means are provided on the needle mount to assist in spring biasing the needle mount in the direction of canting.

In an alternative embodiment withdrawal of the needle mount (and an associated needle) is performed by the portion of the plunger which cooperates with the needle mount being released from a main body portion of the plunger whereupon the needle mount is retracted into the barrel by means such as a spring or vacuum within the plunger.

Additionally, or alternatively in a further embodiment, the plunger, after it has captured the needle mount and been withdrawn at least sufficiently to ensure that the syringe needle no longer projects from the exterior of the syringe, is prevented from further travel in a direction towards the forward end of the barrel. This can be achieved by providing a one-way ratchet mechanism between the plunger and barrel or a snap lock facility between the rearward end of the barrel and the shaft of the plunger adjacent its head. Such a facility may double as the above mentioned means to prevent removal of the plunger from the barrel.

Three embodiments of syringes in accordance with the invention will now be described by way of example only with reference to the accompanying not to scale, schematic drawings in which:

BRIEF DESCRIPTION OF THE DRAWINGS

FIG. 6 is a partial sectional side view of the third embodiment, as the plunger approaches its fully withdrawn position;

FIG. 7 is a similar view to FIG. 6 but with the plunger fully withdrawn and restrained from further movement; and FIG. 8 is a sectional plan view through line A—A of FIG. 7.

DETAILED DESCRIPTION OF THE DISCLOSURE

Figure 1:
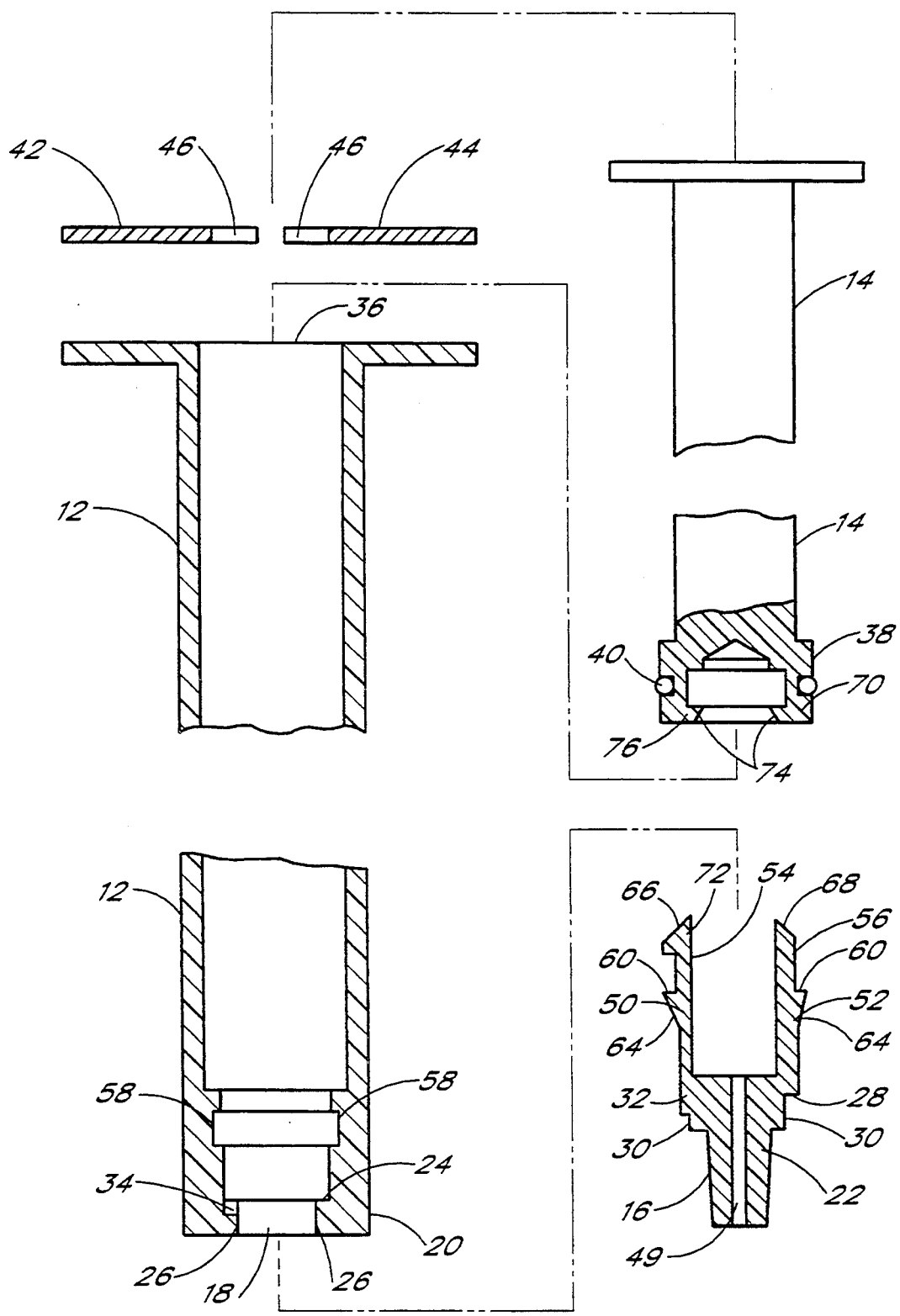
FIG. 1 is a sectional side view of a first embodiment prior to assembly.
Figure 2:
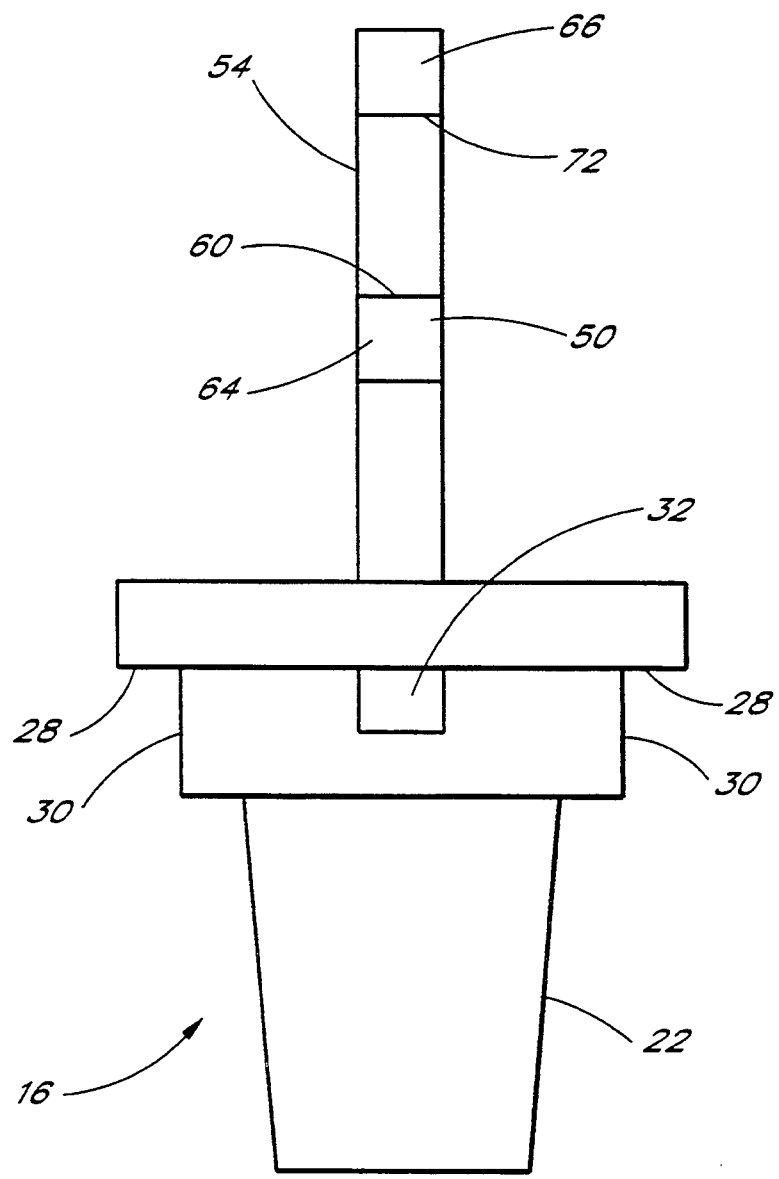
FIG. 2 is a side view of the needle mount of FIG. 1 but rotated 90°.
Figure 3:
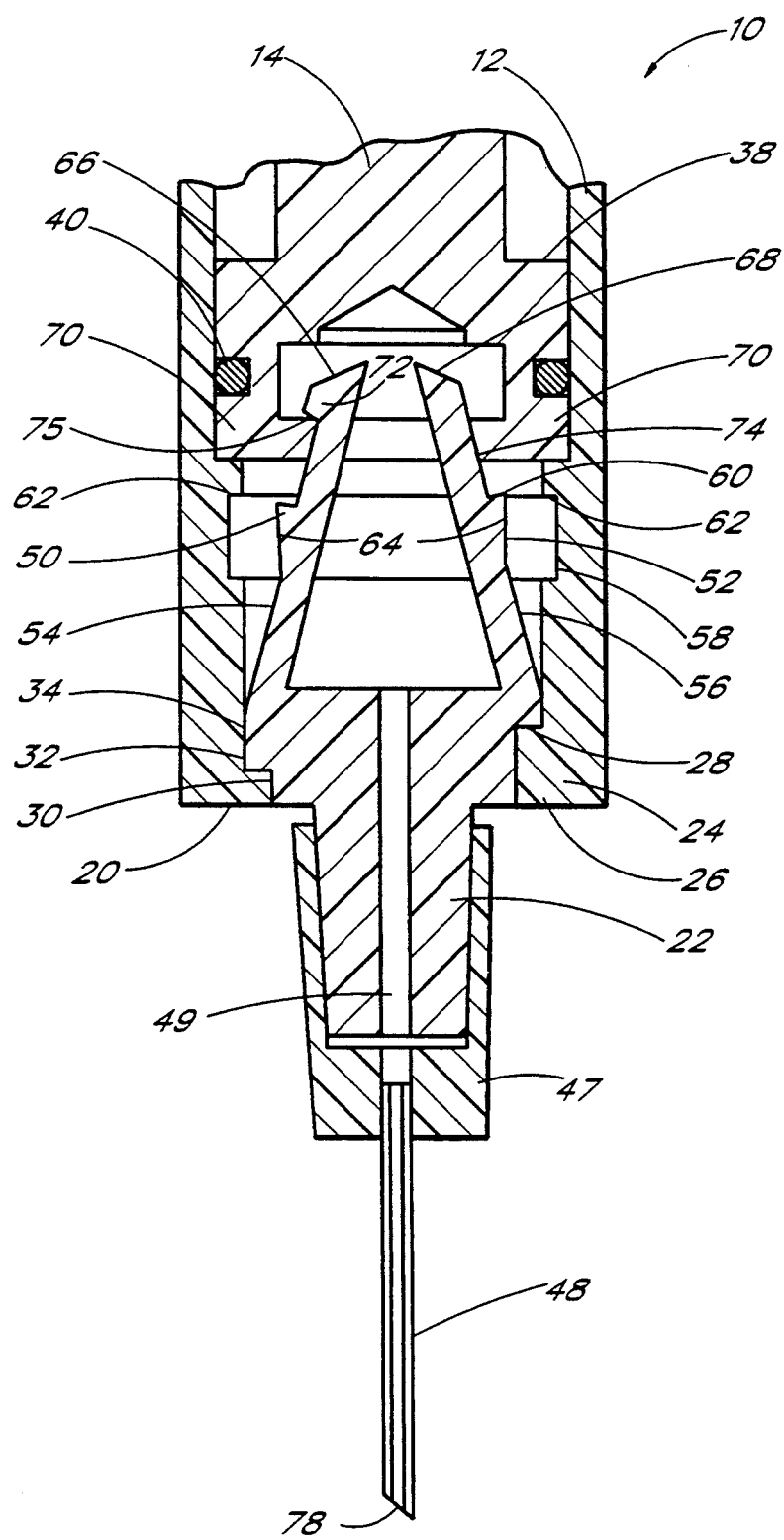
FIG. 3 is a partial sectional side view of the assembled first embodiment as the plunger approaches the needle mount.

Referring initially to FIGS. 1 to 4, the first embodiment 10 of the syringe comprises a barrel 12, a plunger 14 operable within the barrel and a needle mount 16 disengageably securable within an aperture 18 at one end 20 of the barrel. As seen in FIG. 3, when the needle mount is in its engaged position at the said one end 20 of the barrel, a frustoconical needle seat portion 22 extends through the aperture 18, the remainder of the needle mount being restrained from emerging out through the aperture by an annular restraining flange 24 extending inwardly from the interior of the barrel at the said one end 20 to define the rim 26 of the aperture 18. The restraining flange 24 abuts a cooperating annular shoulder 28 extending around the needle mount when the needle mount is in place within the said one end 20 of the barrel whereupon the rim 26 is in fluid tight interference fit relationship with the adjacent exterior wall 30 of the needle mount. As best seen in FIG. 2, a boss 32 extends outwardly from a portion of the interference fit exterior wall 30 of the needle mount adjacent the shoulder 28 thereof. The boss 32 engages a cooperating axially extending groove 34 in the rim 26 of the aperture 18 to prevent the rotation of the needle mount relative to the barrel when in position at the said one end of the barrel.

To assemble the syringe the needle mount is inserted into the barrel from an aperture at a second end 36 of the barrel and snap locked into position at the said one end 20 of the barrel to partially extend through the aperture 18. The head 38 of the plunger is then inserted into the barrel whereupon its sealing means, in this case an O-ring seal 40, allow the plunger to be operable to expel fluid through the aperture 18. After insertion of the head of the plunger, a pair of cover plates 42 and 44 each having a respective semi-circular cutaway 46 are secured across the said second end 36 of the barrel, for instance by ultrasonic welding such that the cutaways cooperate to define an aperture of a narrow diameter than the barrel with the body of the plunger extending therethrough (not depicted). Thus the cover plates prevent complete withdrawal of the plunger from the barrel as the wider head 38 of the plunger will strike the rim of the aperture defined by the cutaways 46 as the head approaches the said second end of the barrel.

The needle mount and its snap lock engagement within the barrel will now be described in greater detail. The frustoconical projection 22 which projects through the aperture 18 at the end 20 of the barrel can receive the plastic seat 47 of a hypodermic needle 48 (not depicted in FIG. 1). The needle communicates with the barrel through a conduit 49 in the needle mount. The needle mount is disengageably locked within the said one end 20 of the barrel by snap lock fittings 50 and 52 each disposed on a respective resilient arm 54 or 56 integrally extending axially along the interior surface of the barrel. The snap lock fittings 50 and 52 each engage a groove 58 extending annularly around the internal surface of the barrel to lock the needle mount within the said one end 18 of the barrel. A cooperating surface 60 of each snap lock fitting is defined perpendicular to the axis of the barrel as does its cooperating shoulder 62 on the groove 58 thereby to prevent displacement of the needle mount unless the arms 54 or 56 are intentionally displaced away from the interior wall of the barrel. An opposed surface 64 of each snap lock fitting is inclined thereby to assist in inserting the needle mount into engagement at the said one end of the barrel during assembly of the syringe.

Each of the arms 54 and 56 extends beyond its respective snap lock fitting, remote from the needle mount, to define a respective inclined surface 66 or 68 each of about 40° relative to the axial direction of the barrel and facing generally towards the adjacent portion of the interior wall of the barrel.

In use, as the plunger is depressed and approaches the needle mount, an annular web 70 extending axially from the fluid contacting face of the plunger engages each inclined surface 66 and 68 of the arms 54 and 56 of the needle mount and thereby displaces the arms 54, 56 towards the interior of the barrel. This causes the snap lock fittings 50 and 52 to disengage from the groove 58, as best seen in FIG. 3. The annular web 70 of the plunger has an inclined internal surface portion 74 of about 30° relative to the axial direction of the barrel to cooperate with the respective inclined surfaces 52 and 54 in displacing the arms 54 and 56.

In order to be able to retract the needle mount 16 with its attached hypodermic 48, an outward facing catch 72 is provided adjacent the free end of one of the arms extending from the needle mount. The catch 72 is gripped by a cooperating catch 74 defined by a radially extending flange 76 extending inwardly from the free end of the annular web 70 after the inclined surface portion 74 which in this embodiment is borne by the radially extending flange 76 has displaced the arms extending from the needle mount sufficiently to unlock their snap lock fittings. When the plunger is subsequently withdrawn into the barrel, the grip of the catches causes the now disengaged needle mount to also be withdrawn into the barrel.

Figure 4:
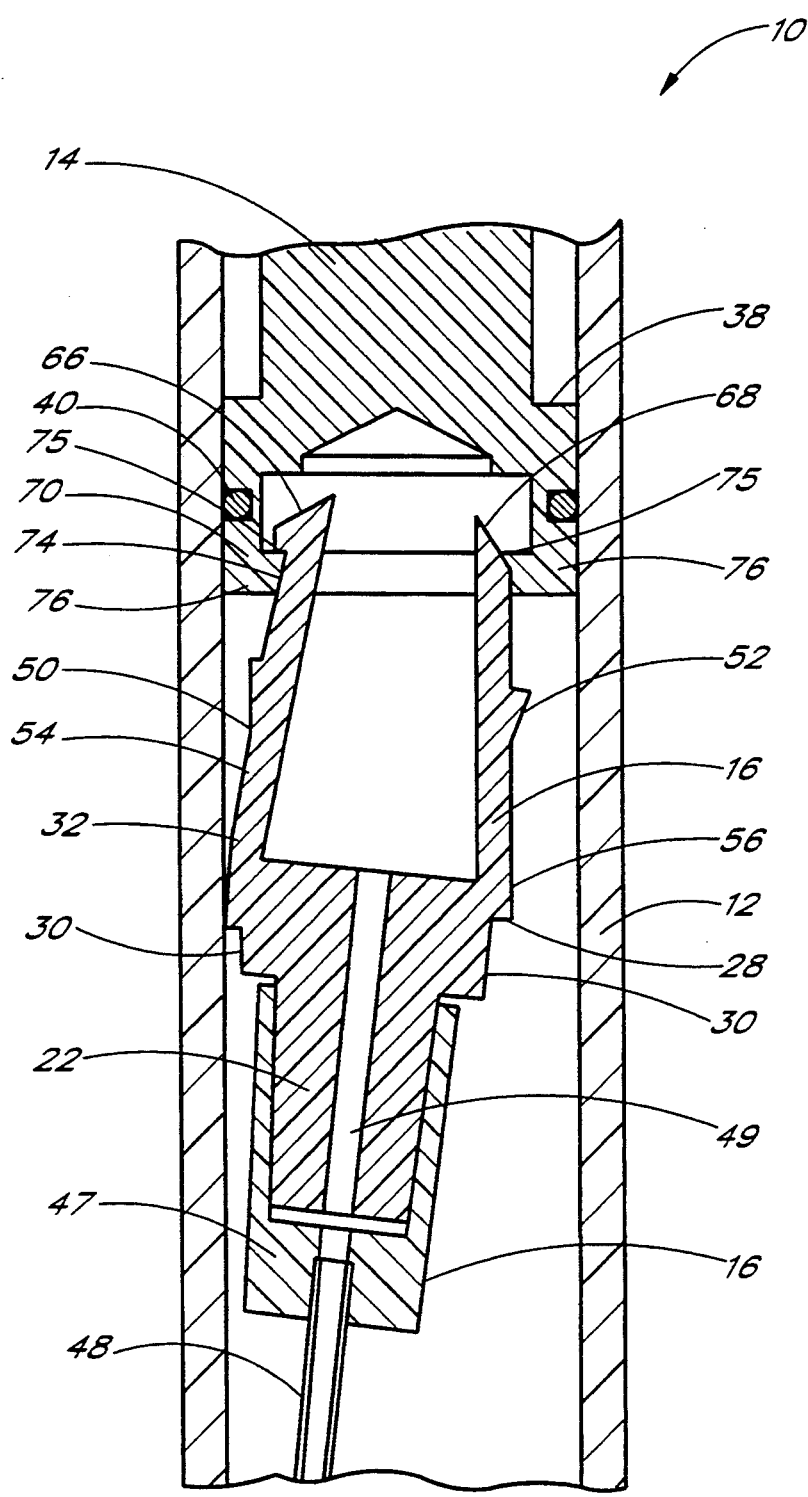
FIG. 4 is a partial sectional view of the assembled first embodiment with the needle mount disengaged from the end of the barrel and withdrawn into the barrel.

In this embodiment 10 only a single catch 74 is provided on the needle mount, on arm 54, and therefore as the retracted needle mount clears the rim 26 of the aperture in the barrel, the needle mount cants over as shown in FIG. 4, in part assisted by the spring bias of the other arm 56 which does not have a catch. When the hypodermic 48 has been entirely withdrawn into the barrel of the syringe, its sharp tip 78 will lie against the interior wall of the barrel and will thus be unable to reissue through the aperture 18 in the barrel if the plunger is re-depressed as its sharp tip is held against the barrel wall by the spring bias of arm 56.

Figure 5:
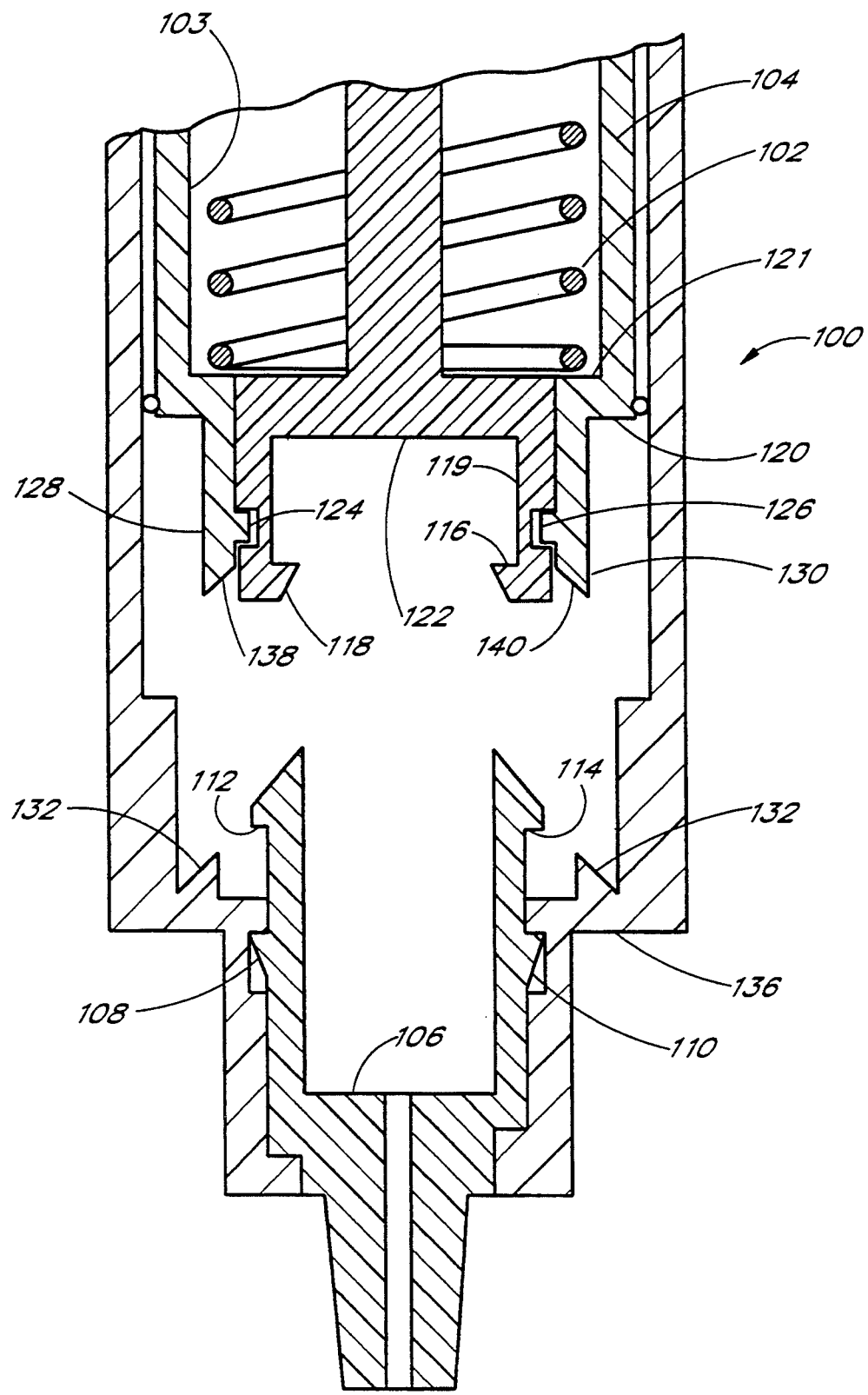
FIG. 5 is a partial sectional side view of a second embodiment having a spring loaded mechanism for withdrawing the needle mount into the body of the plunger.

A portion of the second embodiment 100 of the syringe is depicted in FIG. 5. This embodiment employs a spring 102 disposed within the body 103 of the plunger 104 to retract the needle mount 106 and attached needle into the body of the plunger when the snap lock fittings 108, 110 of the needle mount are disengaged analogously to the embodiment of FIGS. 1 to 3. The only difference in the needle mount relatives to the first embodiment is that a catch 112 or 114 is provided on both arms extending from the needle mount to grip a catch 116 defined by a flange 118 extending inwardly from an annular web 119 which itself extends axially from a central portion 122 of the fluid contacting surface 120 of the plunger.

Prior to retraction of the needle mount, the spring 102 is under tension and extends between a rim 121 behind the fluid contacting surface 120 of the plunger and the rear end (not shown) of the central portion 122 of the plunger. The axially extending annular web 119 to displace the arms of the needle mount is borne on the central portion 122 of the plunger. The central portion 122 is disengageably secured to the fluid contacting end 120 of the plunger by a pair of catches 124, 126 each extending from a respective axially extending arm 128 or 130 disposed on the fluid contacting surface of the plunger outwardly of the central portion 122. The catches 124, 126 each engage a respective detent on a radially outward surface of the annular web 119.

To disengage the catches 124, 126 and allow the spring to withdrew the needle mount into the body of the plunger, an annular inclined projection 132 extends axially towards the plunger from a constricted portion 136 of the barrel adjacent its aperture end.

As the plunger approaches the needle mount, the inclined surface or projection 132 serves to displace a respective cooperating inclined surface 138 or 140 disposed at the free end of each of the arms 128, 130 which secure the central portion 122 of the plunger. As the arms 128, 130 are displaced outwardly, the catches 124, 126 disengage and the needle mount is spring retracted into the body of the plunger, after its snap lock fittings are disengaged by the action of the plunger as described for the embodiment of FIGS. 1 to 3, is spring retracted into the body of the plunger.

Referring now to FIGS. 6 to 8, a third embodiment is depicted in which the plunger, after it has captured and withdrawn the needle mount into the barrel, is locked into position in its fully withdrawn position. Locking of the plunger in this manner prevents the plunger being re-depressed to reissue the captured needle and needle mount through the forward end of the barrel. As the needle mount (and associated needle) are effectively locked at the rearward end of the syringe, it is not essential to employ the arrangement described in FIGS. 1 to 4 to cant the needle over retraction. Thus the asymmetric needle mount 16 depicted in FIGS. 1 to 4 or the biaxially symmetric needle mount of the embodiment of FIG. 5 may each be used with the plunger locking facility depicted in FIGS. 6 to 8.

As shown in FIGS 6 to 8, the plunger may be locked in the fully withdrawn position by providing a plurality of resilient fingers 152 extending into the barrel 154 at the rearward end 156 of the barrel. In this embodiment, the shaft 158 of the plunger has a conventional X shaped profile and, as best seen in FIG. 7, the fingers 152 each project between the ribs 160 defining the X profile. Each finger 152 has a securing portion 162 adhered to a respective finger tab 164 of the syringe and a snap lock portion 166 extending towards the plunger head 168 closely adjacent a respective intersection of adjacent ribs 160. Each snap lock portion 164 terminates in a snap lock head 170.

To cooperate with the snap lock fingers, the plunger adjacent its head 172 is provided with laterally extending flanges 178 each provided between adjacent ribs 160 of the shaft 158. Upon withdrawal of the plunger, the snap lock portion 166 of each finger 152 deforms around and locks a respective flanged 178 to prevent redeployment of the plunger and reissue of the needle through the aperture from which it was withdrawn.

Although the syringe has been described by reference to embodiments having two arms integrally extending from the needle mount it will be readily apparent that other configurations of the securing means for the needle mount, its seating within the end of the barrel and the engagement of the plunger with the needle mount are within the spirit and scope of the invention.

What is claimed is:

1. A syringe comprising:
    a barrel;
    a plunger operable within the barrel;
    a needle mount having a deformable securing portion to disengageably retain the needle mount within one end of the barrel, the securing portion comprising a first element of snap lock engaging means defined by a plurality of resilient angularly spaced arms projecting into the barrel from said one end, each arm having a respective first snap lock element on a radially outward surface thereof which snap lock element engageably cooperates with a second element of the snap lock engaging means on an interior wall of the barrel to provide said disengageable retention;
    means on the plunger to deform the resilient angularly spaced arms as the plunger approaches the needle mount thereby to disengage the snap lock engaging means from the barrel; and
    cooperable means on the plunger and on the needle mount whereby the plunger is capable of engaging the disengaged needle mount for withdrawal of the needle mount into the barrel when the plunger or a portion thereof engaged with the needle mount is displaced away from said one end of the barrel.

2. A syringe according to claim 1 wherein the deforming means on the plunger is defined by a radially inwardly facing inclined surface which is adapted to cooperate with the securing portion to deform the securing portion radially inwardly away from the interior surface of the barrel thereby to disengage the snap lock engagement of the needle mount with the barrel.

3. A syringe according to claim 1 wherein the securing portion comprises a radially outwardly facing inclined end face which is adapted to cooperate with the deforming means on the plunger to disengage the snap lock engagement of the needle mount with the barrel.

4. A syringe according to claim 1 wherein the first and second snap lock elements each have respective cooperating surfaces oriented perpendicular to a longitudinal of the barrel.

5. A syringe according to claim 1 wherein the cooperable means comprises catch means disposed on the securing portion to engage cooperating catch means disposed on the plunger.

6. A syringe according to claim 1 wherein the needle mount defines a seat to detachably receive a needle and wherein a needle engaged with the needle mount is also withdrawable into the barrel with the needle mount.

7. A syringe according to claim 1 wherein one of the needle mount and the interior surface of the barrel has a projection extending radially therefrom and received within an axially extending groove disposed in the other of the needle mount and interior surface thereby to prevent relative rotation between the needle mount and the barrel when the needle mount is retained at said one end of the barrel.

8. A syringe according to claim 1 wherein the plunger, after it has captured and withdrawn the needle mount into the barrel, is prevented from further travel in a direction towards said one end of the barrel.

9. A syringe according to claim 8 wherein means to prevent said further travel comprises a first snap-lock component on the barrel at an opposite end to said one end and a second snap-lock component on the plunger, said first and second snap-lock components of the preventing means cooperating when the plunger has withdrawn the needle mount into the barrel.

10. A syringe according to claim 1 wherein said one end of the barrel has an opening therethrough in which said needle mount is disengageably retained by said snap lock engagement of the securing portion and barrel, and wherein said opening is partly defined by a shoulder on which the needle mount sits when the needle mount is disengageably retained within said one end of the barrel, the shoulder preventing withdrawal of the needle mount outwardly through said opening.

11. A syringe comprising:
    a barrel having an opening therethrough at one end, said opening being partly defined by a shoulder;
    a plunger operable within the barrel towards and away from said one end of the barrel;
    a needle mount disengageably retained within said opening against said shoulder whereby said shoulder prevents withdrawal of the needle mount outwardly through said opening;
    a needle seat on the needle mount, the needle seat being defined by a surface of the needle mount which projects from the barrel opening whereby a needle can be engaged with and disengaged from the needle mount while the needle mount is retained within said opening;
    a deformable securing portion on the needle mount which comprises a first element of snap-lock engaging means defined by two resilient angularly-spaced arms projecting into the barrel from said one end, each arm having a respective first snap lock element on a radially outward surface thereof which snap lock element engagedly cooperates with a fixed element of the snap-lock engaging means on an interior wall of the barrel to provide said disengageable retention;

means on the plunger to deform the resilient angularly spaced arms as the plunger is displaced towards the needle mount thereby to disengage the snap lock engagement of the needle mount with the barrel;

cooperable means on the plunger and on the needle mount whereby the plunger captures the disengaged needle mount for withdrawal of the needle mount into the barrel when the plunger engaged with the needle mount is displaced away from said one end of the barrel; and cooperable snap-engaging means on the plunger and on the barrel to prevent further displacement of the plunger towards said one end of the barrel after the plunger has captured and withdrawn the needle mount into the barrel.

* * * * *